United States Patent [19]

Kownurko

[11] Patent Number: 4,708,017
[45] Date of Patent: Nov. 24, 1987

[54] FLOATING HYDROMETER WITH ENERGY DISSIPATING BAFFLE

[75] Inventor: William A. Kownurko, Bryan, Tex.

[73] Assignee: Combustion Engineering, Inc., Windsor, Conn.

[21] Appl. No.: 879,766

[22] Filed: Jun. 27, 1986

[51] Int. Cl.$^4$ .................... G01N 9/10; G01N 15/06
[52] U.S. Cl. ..................................... 73/438; 73/61 R
[58] Field of Search ................. 73/438, 439, 444, 445, 73/447, 448, 32 R, 61 R

[56] References Cited

U.S. PATENT DOCUMENTS

| | | | |
|---|---|---|---|
| 2,198,351 | 4/1940 | Thielers et al. | 73/438 |
| 2,354,847 | 8/1944 | Woodbridge | 73/438 |
| 3,399,573 | 9/1968 | Ponsar | 73/438 |

Primary Examiner—John Chapman
Attorney, Agent, or Firm—Arthur E. Fournier, Jr.

[57] ABSTRACT

An instrument (10) particularly suited for use for purposes of measuring the presence of suspended solids in a slurry. The subject instrument (10) is comprised of a floating probe portion (12), a long tubular member (14) and an energy dissipating baffle (16). The tubular member (14) is suitably attached to the floating probe portion (12) by virtue of having one (18) of its ends affixed to the middle of the floating probe portion (12). The energy dissipating baffle (16) which is suitably mounted in supported relation to the other end (20) of the tubular member (14) preferably is in the form of a cylindrical member (24) that is divided internally into essentially three chambers (26,28,30) by means of two deflector plates (32,34). The two deflector plates (32,24) are each perforated (36) and are mounted within the interior of the cylindrical member (24) so as to be inclined relative to the longitudinal axis of the cylindrical member (24). Positioned in juxtaposed relation to each of the two deflector plates (32,34) is an opening (36,38) that is formed through the wall of the cylindrical member (24) so as to be operative as a passageway for liquid entering or leaving the cylindrical member (24).

10 Claims, 7 Drawing Figures

FLOATING HYDROMETER WITH ENERGY DISSIPATING BAFFLE

BACKGROUND OF THE INVENTION

This invention relates to instruments, and more specifically to an instrument which based on a theory that two columns of liquid with two different densities and a common pressure reference point will have two different column levels is operative to measure the presence of suspended solids in a fluid substance.

One of the important parameters in many processes is that of the extent to which there are particles present in a fluid substance. As such, it has long been known in the prior art to provide instruments that are capable of being employed for purposes of effecting measurements of particles. To this end, the prior art is replete with examples of various types of instruments that have been utilized heretofore for purposes of obtaining particle measurements. In this regard, in many instances discernible differences exist in the technique by which the measurement of the particles is accomplished. The existence of such differences is, in turn, attributable for the most part to the diverse functional requirements that are associated with the specific application in which such instruments are intended to be employed. For instance, in the selection of the particular type of instrument that is to be utilized for a specific application one of the principal factors to which consideration must be given is that of the nature of the substance of which the particle that is to be measured is composed. Another factor to which consideration must be given is that of the nature of the substance in which the particles are present at the time they are being measured. Yet another factor to which consideration must be given is the relative size of the particles that are to be measured.

Some of the techniques that have been utilized heretodate by the prior art for purposes of accomplishing the measurement of particles include acoustical techniques, optical counting techniques, electrical counting techniques, sedimentation techniques, separation techniques, and surface measurement techniques. Moreover, the kinds of particles with which such techniques have been sought to be applied for purposes of making measurements of the particles include such particles as mineral particles, chemical particles, food particles, blood particles as well as others. In addition, diverse ones of the techniques to which reference has been had hereinbefore have been sought to be employed for purposes of accomplishing the measurement of particles while the latter are present in a variety of different types of fluid substances such as various types of liquids and various types of gases.

One type of process in which the amount of particles that are present in a fluid substance is known to be an important consideration for the successful operation of the process is that process which is utilized in conjunction with wet scrubber applications. In such applications, there exists a need to know to what extent particles are present in a limestone slurry. To this end, there is a need to be able to measure the percent of suspended solids that are present in the limestone slurry. One instrument that those in the prior art have attempted to utilize for purposes of measuring the percent of suspended solids that are present in the limestone slurry is that referred to in the industry as a hydrometer and more specifically as a floating hydrometer. The floating hydrometer works on a theory that two columns of liquids with two different densities and a common pressure reference point will have two different column levels. This theory can be made to work with limestone slurry because if the slurry is not agitated the suspended solids, which make up the majority of the solids, will precipitate out of the liquid such that the liquid which remains has almost the same density as clear water.

Insofar as the nature of the construction thereof is concerned, the floating hydrometer basically resembles a float having a long piece of pipe or cylinder stuck through the middle thereof. The object which is sought to be achieved therewith is to have the pipe or cylinder, by virtue of its relatively long length, function to eliminate agitation of the liquid to a sufficient extent that the suspended solids will fall out of the bottom of the pipe or cylinder. At the top of the pipe or cylinder there is mounted a level probe. Thus, by knowing the level at which the float sits on the liquid, the length of the pipe or cylinder and the densities of the liquid inside and outside of the pipe or cylinder, a difference in level read by the level probe can be calculated for a desired change in percent solids.

Unfortunately, however, when measurements were sought to be made with a floating hydrometer that embodies the form of construction and the mode of operation, which has been described hereinbefore, the results that were obtainable therewith were found to be unacceptable. Namely, it was found that the measurements obtained through the use of such a floating hydrometer were inconsistent. That is, it was found that the measurements obtained through the use of such a floating hydrometer were not consistent when compared to the actual solids known to be present in the reaction tank wherein measurements were sought to be made of the percent of suspended solids in the limestone slurry.

In an effort to overcome this problem of inconsistent measurements being obtained when the floating hydrometer was used to measure the percent of suspended solids in the limestone slurry, one thing which was attempted was that of purging the float, as the latter was being lowered into the reaction tank, for a period of several hours with clean water so as to wash out therefrom any solids that might otherwise be present. Upon trying this, it was found that when the purge water was shut off, the measurements obtained with the floating hydrometer would track the actual reaction tank solids relatively closely for several hours. After some time, however, the floating hydrometer would once again begin to produce erratic measurements that did not correlate with the actual solids in the reaction tank. The extent of the discrepancy which existed between the measurements obtained with the floating hydrometer and the actual solids in the reaction tank appeared to vary depending on the level of the fluid substance in the reaction tank and the number of spray pumps in service in the primary reaction tank.

There were thought to be two possible reasons why the measurements obtained through the use of a floating hydrometer that embodies the nature of the construction and the mode of operation which has been described hereinbefore were found to be inconsistent. The first is thought to reside in the fact that the constant up and down motion, i.e., bobbing, of the floating hydrometer caused by the choppy surface that exists in the reaction tank could conceivably produce sufficient agitation inside the pipe or cylinder of a floating hydrometer to keep suspended solids present in the liquid that is contained within the pipe or cylinder of the floating hydrometer. The other possible explanation for the erratic measurement is that a high volume of liquid flowing at a ninety degree angle past the bottom end of the pipe or cylinder of the floating hydrometer could pull a slight negative pressure inside the pipe or cylinder of the floating hydrometer. The existence of such a slight negative pressure within the pipe or cylinder of a floating hydrometer would tend to lower the internal column height of the liquid therewithin and thereby give rise to erroneous outputs from the floating hydrometer. In this connection, the spray pumps associated with a reaction tank wherein measurements of the percent suspended solids in limestone slurry are sought to be obtained are known to be operative to pump at a rate of 18,500 gallons per minute. Thus, with four pumps in service in a reaction tank, there could very possibly be enough flow past the bottom end of the pipe or cylinder of the floating hydrometer to cause such a condition to exist wherein a slight negative pressure was produced within the pipe or cylinder of the floating hydrometer.

A need has, therefore, been evidenced in the prior art for a new and improved form of floating hydrometer of the type that is operative based on a theory that two columns of liquid with two different densities and a common pressure reference point will have two different column levels. Further, a need has been evidenced for such a new and improved floating hydrometer which would not suffer from the problem of inconsistent measurements that heretodate has served to disadvantageously characterize the performance of prior art forms of floating hydrometers. Moreover, a need has been evidenced for such a new and improved floating hydrometer that would be capable of operation to dissipate the fluid energy occasioned by the bobbing motion to which the float portion of the floating hydrometer is known to be subjected when positioned within a reaction tank. In addition, a need has been evidenced for such a new and improved floating hydrometer that would also be capable of operation as a vacuum break whereby should a slight negative pressure be produced within the floating hydrometer, there will be made to occur an equalization of this negative pressure.

It is, therefore, an object of the present invention to provide a new and improved form of instrument suitable for use for purposes of measuring the presence of particles in a fluid substance.

It is another object of the present invention to provide such an instrument which is particularly suited for employment for purposes of obtaining measurements as to the percent of suspended solids that are in a limestone slurry.

It is still another object of the present invention to provide such an instrument wherein the instrument comprises a floating hydrometer.

A further object of the present invention is to provide such a floating hydrometer which works on the theory that two columns of liquid with two different densities and a common pressure reference point will have two different column levels.

A still further object of the present invention is to provide such a floating hydrometer which is advantageously characterized by the fact that consistent measurements can be obtained through the use thereof notwithstanding the effects of fluid energy.

Yet another object of the present invention is to provide such a floating hydrometer which is advantageously characterized by the fact that consistent measurements can be obtained through the use thereof notwithstanding the effects of negative pressure.

Yet still another object of the present invention is to provide such a floating hydrometer which is relatively easy to employ as well as being relatively inexpensive to provide.

SUMMARY OF THE INVENTION

In accordance with the present invention there is provided an instrument that is designed to be employed for purposes of measuring the presence of particles in a fluid substance. More specifically, there is provided an instrument in the form of a floating hydrometer embodying energy dissipating means that is designed to be employed for purposes of measuring the percent of suspended solids in a limestone slurry that is contained in a reaction tank. The subject floating hydrometer includes a float portion, an elongated tubular member and energy dissipating baffle means. The float portion which is designed to float within the reaction tank is operative as an instrument-bearing housing. The elongated tubular member is suitably attached to the float portion by virtue of having one of its ends affixed to the middle of the float portion. At the other end of the elongated tubular member the energy dissipating baffle means is suitable mounted in supported relation thereto. The energy dissipating baffle means comprises a cylindrical member which is internally divided whereby three chambers are essentially formed therewithin. The internal division of the aforesaid cylindrical member is accomplished by mounting two deflector plates in spaced relation one to another within the cylindrical member. To this end, one of the two deflector plates is suitably attached to the inner surface of the cylindrical member so as to project outwardly and downwardly therefrom in a first direction and so as to terminate short of engagement with the opposite portion of the inner surface of the cylindrical member. The other one of the two deflector plates is suitably attached to the inner surface of the cylindrical member so as to project outwardly and downwardly therefrom in a second direction and so as to terminate short of engagement with the opposite portion of the inner surface of the cylindrical member. Each of the two deflector plates is suitably perforated such as to permit the passage therethrough of liquid. With further reference to the aforedescribed cylindrical member, there is provided in juxtaposed relation to each of the two aforereferenced deflector plates an opening that is formed through the wall of the cylindrical member so as to be operative as a passageway for liquid which either is entering or exiting from the cylindrical member.

DESCRIPTION OF A PREFERRED EMBODIMENT

Figure 1:
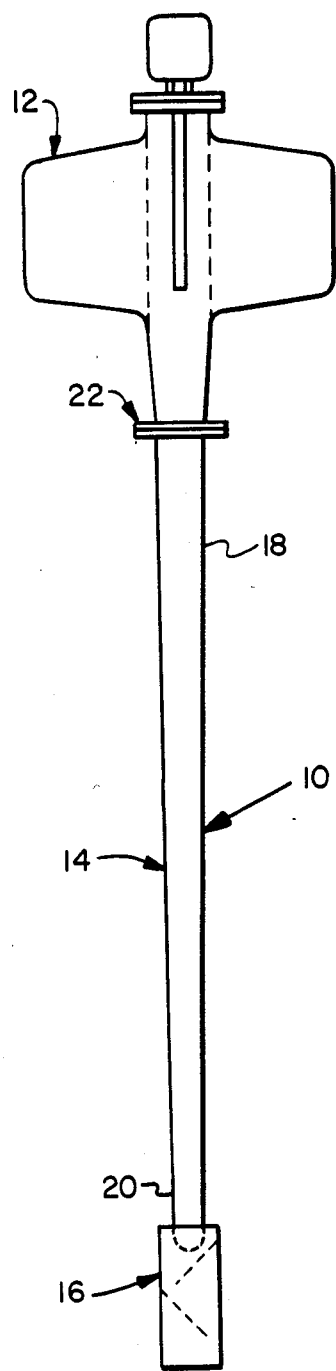
FIG. 1 is a side elevational view of a floating hydrometer embodying an energy dissipating baffle constructed in accordance with the present invention.

Referring now to the drawing, and more particularly to FIG. 1 thereof, there is depicted therein a floating hydrometer with energy dissipating baffle, generally designated by the reference numeral 10, constructed in accordance with the present invention. As illustrated in FIG. 1, the floating hydrometer with energy dissipating baffle 10 is comprised of a float portion, generally designated by the reference numeral 12; an elongated tubular member, generally designated by the reference numeral 14; and an energy dissipating baffle means, generally designated by the reference numeral 16.

Inasmuch as the nature of the construction and the mode of operation of floating hydrometers per se are known to those skilled in the art, it is, therefore, not deemed necessary to set forth herein a detailed description of the float portion 12 and the elongated tubular member 14 that are illustrated in FIG. 1. Rather, it is deemed sufficient for purposes of obtaining an understanding of the nature of the construction and the mode of operation of a floating hydrometer with energy dissipating baffle 10 constructed in accordance with the present invention that the float portion 12 and the elongated tubular member 14 be described herein simply to the extent needed for purposes of acquiring an understanding of the manner in which the energy dissipating baffle means 16 is cooperatively associated therewith in the floating hydrometer with energy dissipating baffle 10 when constructed in accordance with the present invention. Should a more detailed description of the nature of the construction and the mode of operation of the float portion 12 and/or of the elongated tubular member 14 be desired, reference may be had for this purpose to the prior art.

Referring again to FIG. 1 of the drawing, and in particular to the float portion 12 which is depicted therein, the function of the float portion 12, generally speaking, is that of an instrument-bearing housing. To this end, in accord with the best mode embodiment of the invention, the float portion 12 houses a radio frequency capacitance transmitter that is operative in known fashion to provide outputs which are representative of the measurements made with the floating hydrometer with energy dissipating baffle 10 constructed in accordance with the present invention of, for example, the percent of suspended solids in limestone slurry for a wet scrubber application. One such type of radio frequency capacitance transmitter that has been found to be suitable for employment for this purpose is that which is commercially marketed under the trade name "Drexelbrook". As the nomenclature thereof suggests, the float portion 12 is designed to float on the surface of the fluid substance which contains the solids that it is desired to measure by means of the floating hydrometer with energy dissipating baffle 10 constructed in accordance with the present invention. The float portion 12, accordingly, is constructed of material that will float on the surface of a fluid substance. In this regard, any suitable conventional form of material that will enable the float portion 12 to float on the surface of a fluid substance may be employed in the construction of the float portion 12.

There will next be set forth herein a brief description of the elongated tubular member 14. More specifically, there follows hereinafter a description of the elongated tubular member 14 which is deemed to be sufficient to enable one to obtain an understanding of the nature of the construction and the mode of operation of the floating hydrometer with energy dissipating baffle 10 to which the present invention is directed. The elongated tubular member 14, in accordance with the illustration thereof which appears in FIG. 1 of the drawing, comprises a relatively long tubular member 14 that preferably is suitably tapered from the upper end 18 thereof as viewed with reference to FIG. 1 to the lower end 20 thereof also as viewed with reference to FIG. 1. By way of exemplification and not limitation, for those applications wherein the floating hydrometer with energy dissipating baffle 10 is being utilized to measure the percent suspended solids in limestone slurry for a wet scrubber application, the elongated tubular member 14 is made to be approximately eleven feet in length whereas the float portion 12 is made to be approximately four feet in length.

Continuing with the description of the elongated tubular member 14 which is shown in FIG. 1, the elongated tubular member 14 is provided with a hollow interior whereby when the floating hydrometer with energy dissipating baffle 10 is positioned in a tank containing a fluid substance, the fluid substance in known fashion will float into the interior of the elongated tubular member 14. At its upper end 18, as viewed with reference to FIG. 1 of the drawing, the elongated tubular member 14 is suitably attached to the lower end, also as viewed with reference to FIG. 1, of the float portion 12 such as through the use of coupling means, the latter being denoted generally in FIG. 1 by the reference numeral 22. Any conventional form of coupling means suitable for employment in the aforedescribed manner may be utilized for purposes of detachably coupling the elongated tubular member 14 and the float portion 12 together. The other end 20, i.e., the lower end as viewed with reference to FIG. 1, of the elongated tubular member 14 is suitably fastened as will be described more fully hereinafter to the energy dissipating baffle means 16 such as by being welded thereto.

When coupled in the manner described hereinabove, the float portion 12 and the elongated tubular member 14 are designed to be positioned in a tank such as a reaction tank (not shown) containing a fluid substance whereby measurements can be had therewith of the percent solids in the fluid substance such as where the fluid substance comprises limestone slurry for a wet scrubber application and the measurements to be made are those of the percent of suspended solids in the limestone slurry. More specifically, with the float portion 12 and the elongated tubular member 14 coupled together as described hereinbefore, when the combined float portion 12 and elongated tubular member 14 are positioned in a fluid substance for purposes of obtaining measurements therewith of the percent of solids in the fluid substance the mode of operation thereof is such that in a manner well-known to those skilled in the art the float portion 12 floats on the surface of the fluid substance with the elongated tubular member 14 depending therefrom extending downwardly into the fluid substance such that a portion of the fluid substance enters the hollow interior of the elongated tubular member 14 whereby on the theory that two columns of liquid with two different densities and a common pressure reference point will have two different column levels the radio frequency capacitance transmitter housed within the float portion 12 is operative to produce outputs that are representative of the measurements made through the use of the combined float portion 12 and elongated tubular member 14. The aforereferenced theory will work with a fluid substance such as limestone slurry because if the slurry is not agitated the suspended solids which make up the majority of the solids will precipitate out of that portion of the fluid substance which has flowed into the interior of the elongated tubular member 14 whereas the suspended solids will not precipitate out in like fashion from the remainder of the fluid substance in the tank, i.e., the fluid substance that has not flowed into the interior of the elongated tubular member 14. After the suspended solids have precipitated out of the fluid substance that has flowed into the hollow interior of the elongated tubular member 14 the liquid which remains has about the same density as clear water. As such, there exists two columns of liquid, i.e., one within the hollow interior of the elongated tubular member 14 from which the suspended solids have precipitated out and the other within the tank surrounding the outside of the elongated tubular member 14. Moreover, since these two columns of liquids have different densities based on the fact that the suspended solids in the case of the former, i.e., the liquid within the hollow interior of the elongated tubular member 14, has precipitated out of the liquid whereas in the case of the latter, i.e., the liquid within the tank surrounding the outside of the elongated tubular member 14 they have not, and a common pressure reference point exists as defined by the bottommost portion of the elongated tubular member 14, two different column levels of liquid are established, i.e., one inside the hollow interior of the elongated tubular member 14 and the other within the tank in surrounding relation to the elongated tubular member 14. Accordingly, by knowing the level at which the float portion 12 sits in the fluid substance within the tank, the length of the elongated tubular member 14 and the densities of the fluid substance inside and outside of the elongated tubular member 14, it is possible in known fashion by utilizing the instrumentation housed within the float portion 12 to establish the difference in the level of the fluid substance inside and outside of the elongated tubular member 14 and based thereon to calculate a change in the percent of suspended solids in the fluid substance.

When employed in the aforedescribed manner, the combined float portion 12 and elongated tubular member 14 was found to produce inconsistent readings insofar as concerns the measurements made therewith of the percent of suspended solids in limestone slurry for a wet scrubber application. Attempts were made to secure consistent readings with the combined float portion 12 and elongated tubular member 14 but these attempts failed. It was not until the energy dissipating baffle means 16 was cooperatively associated with the combined float portion 12 and elongated tubular member 14 that it was found to be possible to obtain consistent readings with respect to the measurements made of the percent of suspended solids in limestone slurry for a wet scrubber application.

Two reasons why the aforementioned inconsistent readings occurred have been postulated. One possible explanation for the occurrence of the aforesaid inconsistent readings has been attributed to the fact that the constant up and down motion, i.e., bobbing, of the combined float portion 12 and elongated tubular member 14 on the surface of the fluid substance in the reaction tank caused by the choppy surface of the fluid substance within the tank may produce sufficient agitation inside the hollow interior of the elongated tubular member 14 as to keep the solids suspended in the fluid substance that has flowed into the hollow interior of the elongated tubular member 14.

Another possible explanation for the erratic measurements obtained with the combined float portion 12 and elongated tubular member 14 has been ascribed to the fact that a high volume of fluid substance flowing at a ninety degree angle past the lower end 20 of the elongated tubular member 14 could have the effect of causing a slight negative pressure to be induced within the hollow interior of the elongated tubular member 14. Such a slight negative pressure would in turn tend to lower the internal column height of the fluid substance within the elongated tubular member 14, and thereby cause the outputs being produced by the radio frequency capacitance transmitter housed within the float portion 12 to be erroneous. In this connection, the spray pumps associated with a reaction tank wherein measurements of the percent suspended solids in limestone slurry are sought to be obtained are known to be operative to pump at a rate of 18,500 gallons per minute. As such, with four pumps in service in a reaction tank there could very possibly be enough flow past the lower end 20 of the elongated tubular member 14 to cause such a condition to exist wherein a slight negative pressure was produced within the hollow interior of the elongated tubular member 14.

Figure 2:
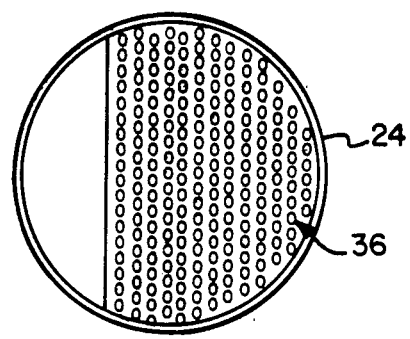
FIG. 2 is a top plan view of the energy dissipating baffle of a floating hydrometer embodying an energy dissipating baffle accordance with the present invention.
Figure 3:
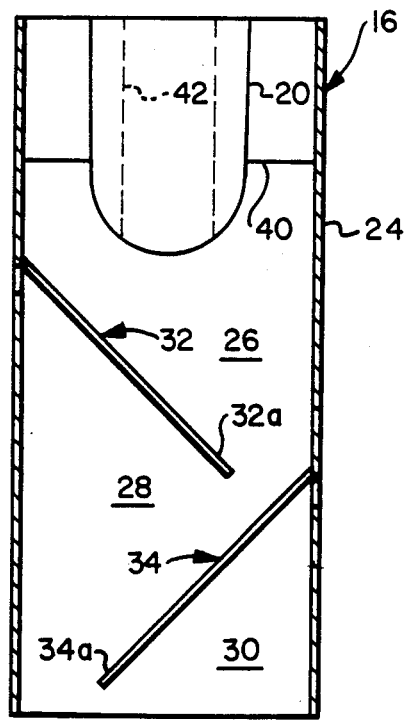
FIG. 3 is a cross-sectional view of the energy dissipating baffle of a floating hydrometer embodying an energy dissipating baffle constructed in accordance with the present invention depicted cooperatively associated with the elongated tubular member of the floating hydrometer embodying an energy dissipating baffle.
Figure 4:
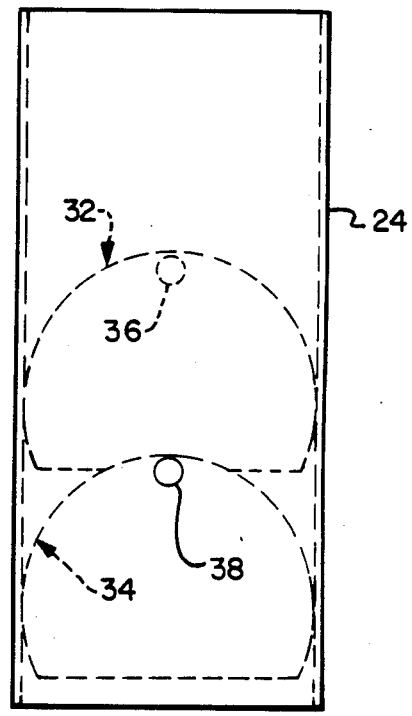
FIG. 4 is a side elevational view of the energy dissipating baffle of a floating hydrometer embodying an energy dissipating baffle constructed in accordance with the present invention.

Reference will now be had in particular to FIGS. 2, 3 and 4 of the drawing for purposes of setting forth hereinafter a description of the nature of the construction of the energy dissipating baffle means, which has generally been designated in FIG. 1 by the reference numeral 16, that in accordance with the present invention is designed to be cooperatively associated with the float portion 12 and the elongated tubular member 14 constructed in the manner illustrated in FIG. 1 so as to produce the floating hydrometer with energy dissipating baffle 10 which comprises the subject matter of the present invention. More specifically, in accord with the present invention the energy dissipating baffle means 16 is operative both to dissipate fluid energy and to function in the manner of a vacuum break. This is accomplished, as will be described more fully hereinafter, by having the energy dissipating baffle means 16 compensate for the up and down, i.e., bobbing, motion of the combined float portion 12 and elongated tubular member 14, and by having the energy dissipating baffle means 16 equalize the pressure should a negative pressure be caused to otherwise occur within the hollow interior of the elongated tubular member 14, respectively.

With further reference to FIGS. 2, 3 and 4, in accord with the best mode embodiment of the invention the energy dissipating baffle means 16 includes a cylindrical member 24 that has the interior thereof divided in a manner yet to be described so as to have formed therewithin three chamber-like areas which for ease of reference have been identified in FIG. 3 of the drawing by the reference numerals 26, 28 and 30, respectively. To this end, the cylindrical member 24 has a pair of deflector plates, denoted generally by the reference numerals 32 and 34, respectively, positioned in spaced relation one to another within the interior thereof. More specifically, as best understood with reference to FIG. 3 of the drawing, the deflector plate 32 is suitably affixed such as by being welded thereto to the inner wall of the cylindrical member 24 at a point located approximately one-third of the length of the cylindrical member 24 measured from the upper end thereof as viewed with reference to FIG. 3 of the drawing, and such that the deflector plate 32 projects outwardly and downwardly from the inner wall of the cylindrical member 24 in a first direction. Furthermore, the deflector plate 32 is suitably dimensioned, i.e., embodies a configuration, such that the free end thereof, denoted by the reference numeral 32a in FIG. 3, terminates short of engagement with the portion of the inner wall of the cylindrical member 24 that lies opposite the point at which the deflector plate 32 is attached to the inner wall of the cylindrical member 24. Lastly, the deflector plate 32, as best understood with reference to FIG. 2, is perforated, i.e., embodies a multiplicity of relatively small openings denoted generally by the reference numeral 36, for the purpose of enabling the fluid substance to pass therethrough.

In a manner similar to that set forth hereinbefore in connection with the description of the deflector plate 32, the deflector plate 34 is suitably affixed such as by being welded thereto to the inner wall of the cylindrical member 24 at a point located approximately one-third of the length of the cylindrical member 24 measured from the lower end thereof as viewed with reference to FIG. 3 of the drawing, and such that the deflector plate 34 which projects outwardly and downwardly from the inner wall of the cylindrical member 24 in a second direction lies in a plane extending substantially perpendicular to the plane in which the deflector plate 32 lies. Likewise, the deflector plate 34 is suitably dimensioned, i.e., embodies a configuration, such that the free end thereof, denoted by the reference numeral 34a in FIG. 3, terminates short of engagement with a portion of the inner wall of the cylindrical member 24 that lies opposite the point at which the deflector plate 34 is attached to the inner wall of the cylindrical member 24. Finally, as best understood with reference to FIG. 2, the deflector plate 34 like the deflector plate 32 described hereinbefore is perforated, i.e., embodies a multiplicity of relatively small openings, for the purpose of enabling the fluid substance to pass therethrough.

Continuing with the description of the nature of the construction of the energy dissipating baffle means 16, the cylindrical member 24 is further provided with a pair of openings, seen at 36 and 38, respectively, in FIG. 4 of the drawing. In accordance with the best mode embodiment of the invention, each of the openings 36 and 38 comprises a hole formed through the wall of the cylindrical member 24 for a purpose that will be described hereinafter. More specifically, the openings 36 and 38 are formed through the wall of the cylindrical member 24 such that the opening 36 is located in juxtaposed relation to the deflector plate 32 slightly below, as viewed with reference to FIG. 3, the point whereat the deflector plate 32 is attached to the inner surface of the cylindrical member 24, and the opening 38 is located in juxtaposed relation to the deflector plate 34 slightly below, as viewed with reference to FIG. 3, the point whereat the deflector plate 34 is attached to the inner surface of the cylindrical member 24. Thus, as can be seen, particularly with reference to FIG. 4 of the drawing, the openings 36 and 38 are suitably positioned so as to be located on opposite sides of the cylindrical member 24 from each other as well as so as to be located at different elevations relative to each other along the length of the cylindrical member 24.

Completing the description of the nature of the construction of the energy dissipating baffle means 16, the latter, as best understood with reference to FIGS. 1 and 3 of the drawing, is designed to be cooperatively associated with the combined float portion 12 and elongated tubular member 14. To this end, the cylindrical member 24 is designed to be mounted in supported relation thereto at the lower end 20 of the elongated tubular member 14. As best understood with reference to FIG. 3 of the drawing, the mounting of the cylindrical member 24 and thus of the energy dissipating baffle means 16 at the lower end 20 of the elongated tubular member 14 preferably is effected through the welding, the latter being identified by means of the reference numeral 40 in FIG. 3, of the lower end of the elongated tubular member 14 to the cylindrical member 24 whereby the hollow interior, denoted by the reference numeral 42 in FIG. 3, of the elongated tubular member 14 is positioned relative to the chamber-like area 26 formed in the cylindrical member 24 so as to be in fluid flow communication therewith. Namely, the upper end, as viewed with reference to FIG. 3, of the cylindrical member 24 is effectively closed off by virtue of the existence of the weld seen at 40 in FIG. 3 except for the fact that the hollow interior 42 of the elongated tubular member 14 is in fluid flow communication with the chamber-like area 26 formed in the cylindrical member 24. On the other hand, the lower end, as viewed with reference to FIG. 3, of the cylindrical member 24 is open. Accordingly, the only way that a fluid substance flowing into the interior of the cylindrical member 24 can leave through the upper end, as viewed with reference to FIG. 3, of the cylindrical member 24 is by flowing into the hollow interior 42 of the elongated tubular member 14.

A description will now be had of the mode of operation of the energy dissipating baffle means 16 from the point of view of the latter being cooperatively associated with the combined float portion 12 and elongated tubular member 14 in the manner depicted in FIG. 1 of the drawing. For this purpose, reference will be had in particular to FIGS. 5, 6 and 7 of the drawing. In this connection note is made here of the fact that as set forth previously herein, the energy dissipating baffle means 16 when cooperatively associated with the combined float portion 12 and elongated tubular member 14 in the manner depicted in FIG. 1 of the drawing has been proven to be operative to overcome the problems that have been found to plague prior art floating hydrometers. The problems to which reference is had here are those relating to the inconsistent readings obtained with the prior art floating hydrometers. Note is further made here of the fact that as has also been previously set forth herein the reason for such inconsistent readings has been postulated to be due either to the failure to dissipate fluid energy, or the failure to prevent a negative pressure from being induced into the interior of the floating hydrometer. To this end, the energy dissipating baffle means 16 constructed in accordance with the present invention is operative both as a means of dissipating fluid energy and as a vacuum break.

Consideration will first be had to the manner in which the energy dissipating baffle means 16 functions as a fluid energy dissipating means. For this purpose reference will be had in particular to FIG. 5 and 6 of the drawing. Continuing, when considering the manner in which the energy dissipating baffle means 16 operates as a fluid energy dissipating means there are two situations which give rise to the must dissipate fluid energy that need to be discussed. One of these occurs when the energy dissipating baffle means 16 is moving in a downwardly direction as can be found depicted schematically in FIG. 5 of the drawing. The other one of these occurs when the energy dissipating baffle means 16 is moving in an upwardly direction as can be found depicted schematically in FIG. 6 of the drawing.

For purposes of the discussion that follows regarding the manner in which the energy dissipating baffle means 16 operates to dissipate fluid energy, it is deemed important to once again note herein the fact that the cylindrical member 24 of the energy dissipating baffle means 16 is divided internally into three chamber-like areas 26, 28 and 30. That is, it is deemed to be important that recognition be taken of the fact that each of the chamber-like areas 26, 28 and 30 has a distinctive role to play insofar as ensuring that the energy dissipating baffle means 16 operates successfully is concerned. To this end, it is the intent, in accord with the mode of operation as a fluid energy dissipating means of the energy dissipating baffle means 16, to have the dissipation of the fluid energy occur within the two lowermost chamber-like areas, i.e., the areas 28 and 30 as viewed with reference to FIGS. 5 and 6, such that the uppermost chamber-like area, i.e., the area 26 as viewed with reference to FIG. 5 and 6, functions as a calm area, i.e., an area wherein the fluid substance undergoes very little, if any, motion. In this connection, it can thus be seen that to the extent that the fluid substance can be made to remain calm in the chamber-like area 26, the fluid substance which is present within the hollow interior 42 will similarly remain calm, i.e., will be unaffected by any agitation of the fluid substance that may occur in the chamber-like area 30 and/or the chamber-like area 28 as the energy dissipating baffle means 16 and thereby also the cylindrical member 24 is caused to move either in a downwardly direction as depicted schematically in FIG. 5 or in an upwardly direction as depicted schematically in FIG. 6.

Figure 5:
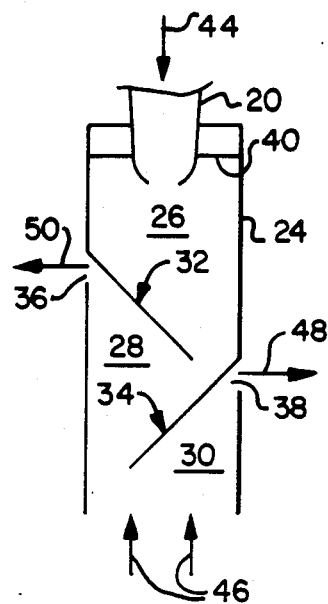
FIG. 5 is a schematic illustration of the energy dissipating baffle of a floating hydrometer embodying an energy dissipating baffle constructed in accordance with the present invention depicting the operation of the energy dissipating baffle when the energy dissipating baffle is undergoing movement in a downwardly direction.

The manner in which the chamber-like areas 28 and 30 function to effectuate the dissipating of fluid energy as the energy dissipating baffle means 16 and thereby also the cylindrical member 24 are being moved in a downwardly direction is best understood with reference to FIG. 5 of the drawing. Referring, therefore, to FIG. 5, as the cylindrical member 24 moves in a downwardly direction as depicted therein by means of the arrow denoted by the reference numeral 44, fluid substance by virtue of this downward movement of the cylindrical member 24 is forced to enter the cylindrical member 24 through the open bottom thereof as depicted schematically in FIG. 5 by means of the arrows denoted therein by the reference numeral 46. After passing into the interior of the cylindrical member 24 the fluid substance encounters the two deflector plates 32 and 34 that as described previously herein are mounted therewithin. In turn the deflector plates 32 and 34 operate to divert the fluid substance in the course of the latter,s upward flow. More specifically, the portion of the fluid substance that encounters the deflector plate 34 is diverted thereby to the opening 38 whereupon the fluid substance passes to the exterior of the cylindrical member 24 through the opening 38 as depicted schematically in FIG. 5 by means of the arrow that is denoted therein by the reference numeral 48. Likewise, the portion of the fluid substance that encounters the deflector plate 32 is diverted thereby to the opening 36 whereupon the fluid substance passes to the exterior of the cylindrical member 24 through the opening 36 as depicted schematically in FIG. 5 by means of the arrow that is denoted therein by the reference numeral 50. As such, from the preceding description it should thus be readily apparent that the fluid substance that enters the cylindrical member 24 through the open bottom thereof as a result of the energy dissipating baffle means 16 being caused to move in a downwardly direction is for the most part made to exit by virtue of the action of the deflector plates 32 and 34 through the openings 36 and 38 to the exterior of the cylindrical member 24 before the fluid substance can reach the chamber-like area 26, i.e., while the fluid substance is still within either the chamber-like area 30 or the chamber-like area 28, such that the fluid substance in the chamber-like area 26 remains essentially unaffected, i.e., little, if any, agitation of fluid substance takes place therewithin, as a result of the passage of fluid substance into the interior of the cylindrical member 24 through the open bottom thereof as the energy dissipating baffle means 16 moves in a downwardly direction as depicted schematically in FIG. 5 of the drawing.

Figure 6:
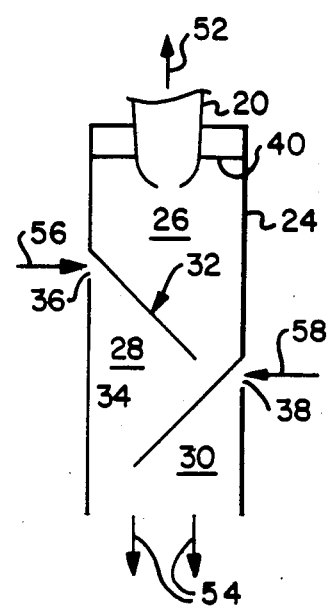
FIG. 6 is a schematic illustration of the energy dissipating baffle of a floating hydrometer embodying an energy dissipating baffle constructed in accordance with the present invention depicting the operation of the energy dissipating baffle when the energy dissipating baffle is undergoing movement in an upwardly direction.

A description will now be had of the manner in which the chamber-like areas 28 and 30 function to effectuate the dissipation of fluid energy as the energy dissipating baffle means 16 and thereby also the cylindrical member 24 is being moved in an upwardly direction as best understood with reference to FIG. 6 of the drawing. With reference, therefore, to FIG. 6, as the cylindrical member 24 moves in an upwardly direction as depicted therein by means of the arrow denoted by the reference numeral 52 a void is created at the open bottom end of the cylindrical member 24 as depicted schematically therein by means of the arrows denoted by the reference numeral 54. This void rather than being filled by fluid substance that is already present within the interior of the cylindrical member 24 is filled by fluid substance that is drawn into the interior of the cylindrical member 24 through the opening 36 as depicted schematically in FIG. 6 by the reference numeral 56 as well as through the opening 38 as depicted schematically in FIG. 6 by the reference numeral 58. It should thus be readily apparent from the preceding description that by virtue of the void, which is created at the open bottom end of the cylindrical member 24 as the energy dissipating baffle means 16 is caused to move in an upwardly direction, being filled by fluid substance entering the interior of the cylindrical member 24 through the openings 36 and 38, the chamber-like area 26 remains essentially unaffected, i.e.. little, if any, agitation of fluid substance takes place therewithin as a result of the void being created at the open bottom end of the cylindrical member 24 when the energy dissipating baffle means 16 is caused to move in an upwardly direction as depicted schematically in FIG. 6 of the drawing.

Figure 7:
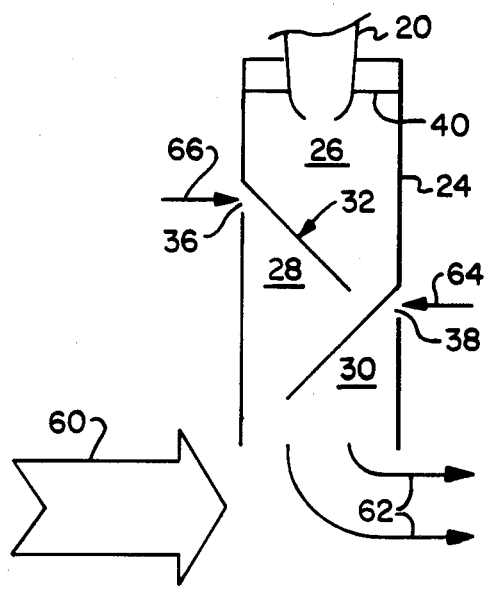
FIG. 7 is a schematic illustration of the energy dissipating baffle of a floating hydrometer embodying an energy dissipating baffle constructed in accordance with the present invention depicting the operation of the energy dissipating baffle when a high volume of liquid flows at a ninety degree angle past the lower end of the energy dissipating baffle.

Next, consideration will be had of the manner in which the energy dissipating baffle means 16 is operative as a vacuum break. For purposes of setting forth herein a description of the manner in which the energy dissipating baffle means 16 is operative as a vacuum break, reference will be had in particular to FIG. 7 of the drawing. To this end, if a large volume of fluid substance moves at a sufficient velocity past the open bottom end of the cylindrical member 24 as depicted schematically in FIG. 7 by the large arrow that is denoted therein by the reference numeral 60, this can in turn result in a negative pressure or a reduced positive pressure being produced within the interior of the cylindrical member 24, a condition which can be found depicted schematically in FIG. 7 by means of the arrows that are denoted therein by the reference numeral 62. In the event that such a condition, i.e., a negative pressure or a reduced positive pressure should be established within the interior of the cylindrical member 24, the energy dissipating baffle means 16 is then operative, in a manner yet to be described, to effectuate the equalization of the aforementioned negative pressure or reduced positive pressure. More specifically, the creation of the negative pressure or reduced positive pressure to which reference is had here occurs within the two lowermost chamber-like areas, i.e., the areas 28 and 30 as viewed with reference to FIG. 7, of the cylindrical member 24. As a consequence thereof, i.e., of the establishment of a negative pressure or a reduced positive pressure within the chamber-like area 30 and/or the chamber-like area 28, fluid substance will be drawn into the interior of the cylindrical member 24 through the opening 38 as depicted schematically in FIG. 7 by the arrow denoted therein by the reference numeral 64 and/or through the opening 36 as depicted schematically in FIG. 7 by the arrow denoted therein by the reference numeral 66. The effect of this flow of fluid substance through the openings 38 and 36 into the interior of the cylindrical member 24 is to create an equalization of the pressure of the fluid substance within the interior of the cylindrical member 24. Moreover, this equalization of the pressure of the fluid substance within the interior of the cylindrical member 24 is designed to occur before the fluid substance that is present in the uppermost chamber-like area, i.e., the area 26 as viewed with reference to FIG. 7 is affected thereby. Namely, as a consequence of a negative pressure or a reduced positive pressure being created within the chamber-like area 30 and/or the chamber-like area 28 resulting from the fact that a large volume of fluid substance moves at a sufficient velocity past the open bottom end of the cylindrical member 24, the chamber-like area 26 in effect functions in the manner of a vacuum break whereby the aforereferenced negative pressure or reduced positive pressure does not have the effect of causing a withdrawal of fluid substance from the hollow interior of the elongated tubular member 14.

In summary, therefore, it should now be readily apparent based on the preceding description of the mode of operation of the energy dissipating baffle means 16 that the latter is operative to cause the chamber-like area 26 to remain substantially calm notwithstanding the fact that the fluid substance within the chamber-like area 28 and/or within the chamber-like 30 may be subjected to agitation. Moreover, this calmness of the fluid substance within the chamber-like area 26 in turn ensures that the fluid substance within the hollow interior of the elongated tubular member 14 will not be affected by any agitation to which the fluid substance within the chamber-like area 30 and/or the chamber-like area 28 may be subjected by virtue of either the failure to dissipate fluid energy, or the failure to prevent a negative pressure from being induced into the interior of the floating hydrometer. That is, the chamber-like area 26 is designed to function in effect as a barrier to insulate the fluid substance that is present within the hollow interior of the elongated tubular member 14 from being affected by whatever affects the fluid substance present within the chamber-like area 28 and/or the chamber-like area 30.

Thus, in accordance with the present invention there has been provided a new and improved form of instrument suitable for use for purposes of measuring the presence of particles in a fluid substance. Moreover, the instrument of the present invention is particularly suited for employment for purposes of obtaining measurements as to the percent of suspended solids that are in a limestone slurry. In addition, in accord with the present invention an instrument is provided which comprises a floating hydrometer. Further, the floating hydrometer of the present invention is characterized in that it works on the theory that two columns of liquid with two different densities and a common pressure reference point will have two different column levels. Additionally, in accordance with the present invention, a floating hydrometer is provided that is advantageously characterized by the fact that consistent measurements can be obtained through the use thereof notwithstanding the effects of fluid energy. Also, the floating hydrometer of the present invention is additionally advantageously characterized by the fact that consistent measurements can be obtained through the use thereof notwithstanding the effects of negative pressure. Furthermore, in accordance with the present invention a floating hydrometer has been provided that is relatively simple to employ as well as being relatively inexpensive to provide.

While only one embodiment of my invention has been shown and described herein, it will be appreciated that modifications thereof, some of which have been alluded to hereinabove, may still be readily made thereto by those skilled in the art. I, therefore, intend by the appended claims to cover the modifications alluded to herein as well as all other modifications which fall within the true spirit and scope of my invention.

What is claimed is:

1. A floating hydrometer employable for purposes of obtaining measurements of the presence of suspended solids in a fluid substance contained in a receptacle comprising:

a. a probe portion operative as an instrument-bearing housing, said probe portion being floatable on the surface of the fluid substance contained in the receptacle;

b. an elongated tubular element having a hollow interior and at least one open end so as to enable the flow into said hollow interior of said elongated tubular element through said open end thereof of fluid substance contained in the receptacle, said elongated tubular element having the other end thereof affixed to said probe portion so as to form an integral structure therewith; and c. energy dissipating baffle means having a first mode of action and a second mode of action and including a member having a hollow interior, said member having one end thereof secured to said open end of said elongated tubular element so as to establish a flow path therebetween for the flow of fluid substance, said member having the other end thereof open so as to enable the flow of fluid substance contained in the receptacle into and out of said hollow interior of said member, said member including a first deflector supported in said hollow interior thereof so as to extend in a first direction and a second deflector supported in said hollow interior thereof so as to extend in a second direction, said first deflector and said second deflector being operative to divide said hollow interior of said member into a first chamber-like area, a second chamber-like area, and a third chamber-like area, said member further including a first aperture formed in said member in juxtaposed relation to said first deflector and a second aperture formed in said member in juxtaposed relation to said second deflector, said energy dissipating baffle means being operative in accord with said first mode of action to cause the flow of fluid substance through said first aperture between said second chamber-like area and the receptacle and through said second aperture between said third chamber-like area and the receptacle so as to thereby effectuate the dissipation of the fluid energy of the fluid substance in said second chamber-like area and of the fluid substance in said third chamber-like area such that the fluid substance in said first chamber-like area remains calm, said energy dissipating baffle means being operative in accord with said second mode of action to cause the flow of fluid substance through said first aperture between said second chamber-like area and the receptacle and through said second aperture between said third chamber-like area and the receptacle so as to thereby effectuate an equalization of the pressure of the fluid substance in said second chamber-like area and of the pressure of the fluid substance in said third chamber-like area such that the fluid substance in said first chamber-like area remains calm.

2. The floating hydrometer as set forth in claim 1 wherein said member is cylindrical in configuration.

3. The floating hydrometer as set forth in claim 2 wherein said first deflector comprises a first deflector plate.

4. The floating hydrometer as set forth in claim 3 wherein said first deflector plate has one end thereof secured to said member and the other end thereof terminating short of engagement with said member.

5. The floating hydrometer as set forth in claim 4 wherein said first deflector plate is supported in said hollow interior of said member so as to lie in a plane extending at an acute angle relative to the longitudinal axis of said member.

6. The floating hydrometer as set forth in claim 5 wherein said second deflector comprises a second deflector plate.

7. The floating hydrometer as set forth in claim 6 wherein said second deflector plate has one end secured to said member and the other end thereof terminating short of engagement with said member.

8. The floating hydrometer as set forth in claim 7 wherein said second deflector plate is supported in said hollow interior of said member in spaced relation to said first deflector plate and so as to lie in a plane extending at an acute angle relative to the longitudinal axis of said member and perpendicular to the plane of said first deflector plate.

9. The floating hydrometer as set forth in claim 8 wherein said first aperture comprises a first opening formed through the sidewall of said member.

10. The floating hydrometer as set forth in claim 9 wherein said second aperture comprises a second opening formed through the sidewall of said member.

* * * * *